(12) United States Patent
Harripersad

(10) Patent No.: US 8,496,948 B2
(45) Date of Patent: Jul. 30, 2013

(54) TOPICAL SKIN COMPOSITION COMPRISING MINERAL YEAST FERMENTS

(75) Inventor: Steve Harripersad, Pompton Lakes, NJ (US)

(73) Assignee: Bath and Body Works Brand Management, Inc., Reynoldsburg, OH (US)

(*) Notice: Subject to any disclaimer, the term of this patent is extended or adjusted under 35 U.S.C. 154(b) by 358 days.

(21) Appl. No.: 12/592,755

(22) Filed: Dec. 2, 2009

(65) Prior Publication Data

US 2011/0129453 A1 Jun. 2, 2011

(51) Int. Cl.
- *A61K 8/02* (2006.01)
- *A61K 36/00* (2006.01)
- *A61K 36/886* (2006.01)
- *A01N 63/00* (2006.01)
- *A01N 65/00* (2009.01)

(52) U.S. Cl.
USPC ....... 424/401; 424/725; 424/93.51; 424/93.1; 424/744

(58) Field of Classification Search
USPC .............. 424/401, 725, 93.51, 93.1, 744
See application file for complete search history.

(56) References Cited

U.S. PATENT DOCUMENTS

| | | | |
|---|---|---|---|
| 5,643,587 A | 7/1997 | Scancarella | |
| 5,840,309 A | 11/1998 | Herstein et al. | |
| 5,958,437 A | 9/1999 | Zaveri | |
| 6,238,678 B1* | 5/2001 | Oblong et al. | 424/401 |
| 6,916,493 B2 | 7/2005 | Morelli et al. | |
| 7,090,860 B2* | 8/2006 | Yousfi et al. | 424/401 |
| 7,094,432 B2 | 8/2006 | Reinhart et al. | |
| 7,291,340 B2 | 11/2007 | Mammone et al. | |
| 7,396,534 B2 | 7/2008 | Bajor et al. | |
| 2006/0018867 A1 | 1/2006 | Kawasaki et al. | |
| 2006/0024339 A1 | 2/2006 | Murad | |
| 2007/0122492 A1 | 5/2007 | Behr et al. | |
| 2007/0134173 A1 | 6/2007 | Tanaka et al. | |
| 2007/0184013 A1 | 8/2007 | Snyder et al. | |
| 2007/0185216 A1 | 8/2007 | Snyder et al. | |
| 2008/0014231 A1 | 1/2008 | Okano | |
| 2008/0300529 A1 | 12/2008 | Reinstein | |
| 2009/0004170 A1 | 1/2009 | Ikehara et al. | |
| 2009/0018213 A1 | 1/2009 | Snyder et al. | |
| 2010/0074857 A1* | 3/2010 | Lipkin et al. | 424/70.7 |

OTHER PUBLICATIONS

Thiel, R., PhD, Doctors' Reasearch, online, URL<http://www.doctorsresearch.com/articles3.html>, accessed May 2, 2012, 16 pages.*

Adina Cosmetic Ingredients, Online, URL<http://www.cosmeticingredients.co.uk/products.asp?prod=979>, accessed May 1, 2012, 2 pages.*

(Continued)

*Primary Examiner* — Patricia Leith
(74) *Attorney, Agent, or Firm* — Andrus, Sceales, Starke & Sawall, LLP

(57) ABSTRACT

A cosmetic composition with superior moisturizing benefits comprising from approximately 0.3% to approximately 0.9% by weight of bio-chelated mineral blend comprising silicon, magnesium, copper, iron, zinc, and calcium, and at least approximately 85.0% by weight of a humectant blend. Preferably, the bio-chelated mineral blend comprise *Saccharomyces* zinc ferment, *Saccharomyces* copper ferment, *Saccharomyces* magnesium ferment, *Saccharomyces* iron ferment, *Saccharomyces* silicon ferment, and *Saccharomyces* calcium ferment in equal amounts, more preferably from approximately 0.05% to approximately 0.15% by weight of each component. The humectant blend preferably comprises glycerin, beet root extract, and *Aloe barbadensis* leaf polysaccharides.

12 Claims, 7 Drawing Sheets

Hydration Level at 4 Hours

OTHER PUBLICATIONS

Flick, E.W. Cosmetic Additives; An Industrial Guide; Noyes Publications, Park Ridge, NJ (1991), p. 98.*

EFSA Journal (2009) 1130, pp. 1-8.*

Cheryl Tiegs Ageless Woman; All Eyes on you; Nourishing eye formula with rejuvacell:online, URL<http://web.archive.org/web/20050509022456/http://www.agelesswomanonline.com/aw_directions.asp> 4 pages.*

Pokaz pelna werje; Online, URL<http://wizaz.pl/forum/archive/index.php/t-154685.html,Cosmetic Review; accessed Jun. 26, 2012, 5 pages.*

Youthful Renewal; Rejuvinate Your Skin for a Younger Appearance; Transform Essence;Online, URL<http://web.archive.org/web/20080926031808/http://www.greenleavesorganics.com/skincare.html> Sep. 26, 2008; 5 pages.*

Swanson Health Products; Viviscal Scalp Lotoion; Online URL< http://www.swansonvitamins.com/VV003/ItemDetail> pp. 1-3, accessed Jun. 26, 2012.*

TotalBeauty: Product Reviews: Avon Planent Spa Icelandic Mineral Waters Purifying Facial Cleanser; Online; URL<http://www.totalbeauty.com/mobile/manufacturerinfo/500384, accessed Jun. 27, 2012, 2 pages.*

Retnam, T. Not Turning a Hair; Malaysian Business; Juala Lumpur: Jan. 16, 2002, p. 82; pp. 1-2 of ProQuest Database.*

PurMinerals: Lemon Mineral Wash; Online, URL<http://www.purminerals.com/Lemon-Mineral-Wash> accessed Jun. 26, 2012, 3 pages.*

J.A. Vinson, et al., "Comparison of the Bioavailability of Trace Elements in Inorganic Salts, Amino Acid Chelates and Yeast", Proceedings on Mineral Elements, 615-621 (1981).

Graemae M. Walker, et al., "Yeast-Metal Interactions: Impact on Brewing and Distilling Fermentations", Institute of Brewing & Distilling Asia Pacific Section 2006 Convention.

Andrzej A. Dlugosz, et al., "Protein Kinase C Regulates Keratinocyte Transglutaminase (TGk) Gene Expression . . . ", Journal of Investigative Dermatology, 102; 409-414 (1994).

Y. Sawada, et al., "Benefits of Silicone Occlusive Dressing for Treatment of Meshed Skin Grafts", Burns, 18(3); 233-6 (Jun. 1992).

Y. Sawada, et al., "Beneficial Effects of Silicone Cream on Grafted Skin", British Journal of Plastic Surgery, 45(2):105-8 (Feb.-Mar. 1992).

P. W. M. Copeman., et al., New Non-Steroid Non-Antibiotic Skin Medicaments, British Medical Journal, 4:264 (Nov. 1, 1975).

S. J. Beveridge, et al., "Lipophilic Copper (II) Formulations: . . . ", Agents and Actions, vol. 12, ½ (1982).

Bunda, et al., "Fluctuations of Intracellular Iron Modulate Elastin Production", The Journal of Biological Chemistry, 280, 2341-2351 (Jan. 21, 2005).

Elizabeth F. Rostan, et al, "Evidence Supporting Zinc as an Important Antioxidant for skin, International Journal of Dermatology", 41(9): 606-611 (Sep. 2002).

M. Iwata, et al., "Zinc Accumulation and Metallothionein Gene Expression . . . ", Histochemistry and Cell Biology, 112(4): 283-290 (Oct. 1999).

Xiangjian Zheng, et al., "Aquaporin 3 Colocates with Phospholipase D2 in Caveolin-Rich Membrane Microdomains . . . ", Journal of Investigative Dermatology, 121, 1487-1495 (2003).

* cited by examiner

TOPICAL SKIN COMPOSITION COMPRISING MINERAL YEAST FERMENTS

FIELD OF INVENTION

The present invention relates generally to a cosmetic composition and method of moisturizing the skin, and particularly to an improved skin moisturizing composition comprising a bio-chelated mineral blend and a high concentration of humectant blend.

BACKGROUND OF THE INVENTION

The skin is the largest organ of the human body. It plays a key role in protecting the body against pathogenic invasion, physical trauma, and excessive water loss. These functions are achieved largely by the outermost layer of the skin called the epidermis. The epidermis is composed of four to five sublayers, of which the stratum corneum is the outer most layer. The stratum corneum contains dead skin cells mixed with natural oils known as lipids, and hydrophilic components that attract water. Lipids are produced by live skin cells in the dermis, a layer underlying the epidermis. Lipids minimize water loss from the stratum corneum and keep chemicals and pathogens from entering the body. Thus, both the lipids and the hydrophilic components are necessary to retain water in the skin.

Properly hydrated stratum corneum makes the appearance of the skin soft, supple, and dewy. However, the stratum corneum can be easily damaged due to various factors, such as friction, weather, chemical irritants, organic solvents, surfactants, and hormonal imbalance. The damage is frequently associated with abnormally high transepidermal water loss (TEWL) (i.e., loss of water from the stratum corneum via diffusion and/or evaporation). Under normal conditions, some TEWL is necessary in order to control the skin's water content and maintain it in dynamic equilibrium with the environment. However, an excessive TEWL causes the skin to become dry, dull, red, and/or flaky. These symptoms are also accompanied by tight, itchy, and/or painful sensations. In more advanced cases, fish net-like cracks or bleeding can occur. If untreated, dry skin can lead to dermatitis, swelling, and infection. Even if the condition is mild, chronically dry skin often results in premature aging of the skin.

Thus, there is a need to effectively hydrate the stratum corneum in order to prevent or repair the aforementioned damage. There are mainly two mechanisms by which the skin can be hydrated: 1) applying a hydrophobic barrier ("film former") to the skin that mimics the function of the endogenous lipids, or 2) applying hydrophilic agents such as humectants to the skin for attracting water.

Traditionally, film formers have been used to minimize TEWL. Hydrophobic lipids such as petrolatum, lanolin, fatty acids, triglycerides, and phospholipids are a few examples of film formers. Popular commercially available products that contain film formers include Aquaphor™ Ointment by Beiersdorf Inc. and Vaseline™ Petroleum Jelly by Unilever. The film formers in these products form an inert, occlusive film or membrane which retards TEWL by preventing water evaporation from the stratum corneum. However, film formers do not replenish moisture in the stratum corneum, but merely provide a surface coating on the skin. In addition, film formers impart a greasy feel to the skin that deters many consumers.

Humectants are used as moisturizers to attract water by mimicking the role of hydrophilic components of the stratum corneum. Examples of popular humectants include glycerin, propylene glycol, and urea. When applied to the skin, humectants are absorbed into the stratum corneum and draw water from both the dermis and the atmosphere. Due to their ability to hold moisture, humectants enable the skin to maintain higher than normal equilibrium moisture content. One drawback of humectants is "tack" or "drag" feel on the skin during or after application. Another, yet more serious, problem is their inability to prevent evaporative water loss from the skin. This drawback becomes prevalent in a dry environment, where moisture escapes into the atmosphere, while the humectants continue drawing water from the deeper layers of the skin. This inadvertently results in increased skin dryness.

In order to prevent undesired water loss, film formers are often combined with humectants. However, this combination often causes surface build-up on the skin, which could become comedogenic (i.e., tending to produce or aggravate acne). Moreover, the combination of humectants and film formers may not always achieve the desired hydration level in the skin, requiring repeated application. This is impractical and uneconomical from the consumers' perspective.

Thus, formulators are now looking for more effective and practical methods to improve hydration. Recently, minerals have been garnering much attention as their health benefits are discovered. Minerals, in a broadest sense, refer to a naturally occurring inorganic elements or compounds with a characteristic chemical composition and structure. They are essential to the nutrition of humans, animals, and plants. Minerals range in composition from pure elements and simple salts to very complex structures with thousands of known forms. Minerals also play an essential role in enzymatic reactions in biological systems. Minerals that are important for cellular function include calcium, iron, copper, zinc, magnesium and silicon. They are often found in commercial supplements as trace nutrients.

An example of prevalent health benefits offered by topical application of minerals is the Dead Sea. The Dead Sea comprises a unique mineral composition, including minerals comprising magnesium, potassium, calcium, and sodium. The combination of minerals in the Dead Sea is known to alleviate many skin ailments such as psoriasis, eczema, and dermatitis. Some experts even claim that washing the skin with mineral water can help reduce common skin irritations and increase the skin cells' ability to absorb moisture. Recently, it has been discovered that certain types of copper peptide complexes possess both tissue protection and repair properties. One example is a human copper peptide complex, glycyl-1-histidyl-1-lysine:copper(II) complex ("GHK-Cu"), developed by Loren Pickart, PhD. Clinical studies have reported improvements in skin elasticity, thickness, and firmness with the use of GHK-Cu. Currently, GHK-Cu is utilized in several anti-aging products available from Neutrogena Corporation, such as Neutrogena Visibly Firm® Night Cream and Neutrogena Visibly Firm® Eye Cream.

Apart from minerals, yeast extracts have been gaining popularity for their ability to improve skin hydration and complexion. In particular, the specific species of yeast *Saccharomyces cerevisiae*, known as the "brewer's yeast," is commonly used for skin care preparations. If processed under proper conditions, the bio-molecules of yeast cells maintain their active forms. These active forms of yeast bio-molecules have been shown to regulate the skin's biochemical pathways in vitro. For example, a composition containing *Saccharomyces* extract is thought to hydrate the skin by stimulating biochemical activities of certain skin cells keratinocyte and fibroblast. (See U.S. Pat. No. 5,840,309). Many consumers report immediate improvement in their skin complexion after using products containing yeast extracts.

Over the past years, the two cosmetic fields of minerals and yeast have merged to produce bio-chelated minerals. Bio-chelated minerals are obtained by growing yeasts in a medium enriched with minerals in the form of inorganic salts. Through a series of growth and division, the yeast culture absorbs and processes the added minerals. The resulting yeast extracts contain the minerals chelated by the yeasts' biomolecules, more commonly known as bio-chelated minerals. Bio-chelated minerals are very diverse, as various combinations of yeast species and minerals are possible. Bio-chelated minerals may contain the same trace elements as their counterpart minerals such as inorganic salts and peptide complexes, but their properties are very different. For example, Vinson, et al. orally administered various forms of minerals to rats to demonstrate that a bio-chelated mineral is the most bioavailable form of trace elements. (J. A. Vinson, et al., *Comparison of the Bioavailability of Trace Elements in Inorganic Salts, Amino Acid Chelates and Yeast*, Proceedings on Mineral Elements, 615-621 (1981)). Moreover, our research has unexpectedly revealed that when a certain combination of bio-chelated minerals and a humectant mixture is applied to the skin, an exceptional hydration of the stratum corneum is achieved. Specifically, a bio-chelated mineral blend containing six minerals (silicon, magnesium, copper, iron, zinc, and calcium) proved to be a superior combination for skin hydration.

SUMMARY OF INVENTION

It is therefore an object of the invention to provide a cosmetic composition comprising a bio-chelated mineral blend and a humectant blend.

It is yet another object of the invention to provide a cosmetic composition comprising minerals with improved skin penetration.

It is another object of the present invention to enhance the skin moisturizing effect of humectants with a bio-chelated mineral blend.

It is another object of the invention to increase hydration of the stratum corneum by applying a moisturizing composition comprising a bio-chelated mineral blend and a humectant blend to the skin.

It is another object of the present invention to provide anti-aging benefits to the skin by applying a composition comprising a bio-chelated mineral blend and a humectant blend to the skin.

The present invention relates to a cosmetic composition comprising up to approximately 1.0% by weight of a bio-chelated mineral blend and at least approximately 85.0% by weight of a humectant blend. Preferably, the bio-chelated mineral blend is present in an amount from approximately 0.3% to approximately 0.9% by weight and the humectant blend is present in at least approximately 89.0% by weight in the cosmetic composition. The bio-chelated mineral blend may comprise six different minerals, preferably those containing silicon, magnesium, copper, iron, zinc, and calcium. The bio-chelated mineral blend is preferably obtained in the form of *Saccharomyces cerevisiae* extracts, separately cultured in an environment containing minerals of silicon, magnesium, copper, iron, zinc, and calcium. The humectant blend may comprise one humectant or more than one humectant. Preferably, the humectant blend comprises from approximately 70.7% to approximately 78.9% by weight of glycerin, from approximately 18.0% to approximately 22.0% by weight of beet root extract, and from approximately 1.0% to approximately 3.0% by weight of *Aloe barbadensis* leaf polysaccharides. The combination of the bio-chelated mineral blend and the humectant blend works synergistically to enhance the skin's hydration level.

BRIEF DESCRIPTION OF THE FIGURES

A further understanding of the present invention can be obtained by reference to a preferred embodiment, along with some alternative embodiments, set forth in the illustrations of the accompanying figures. Although the illustrated embodiments are merely exemplary of systems for carrying out the present invention, the organization and method of operation of the invention in general, together with further objectives and advantages thereof, may be more easily understood by reference to the figures and the following description. The figures are not intended to limit the scope of this invention, which is set forth with particularity in the claims as appended or as subsequently amended, but merely to clarify and exemplify the invention.

For a more complete understanding of the present invention, reference is now made to the following figures.

DETAILED DESCRIPTION OF THE INVENTION

Figure 1:
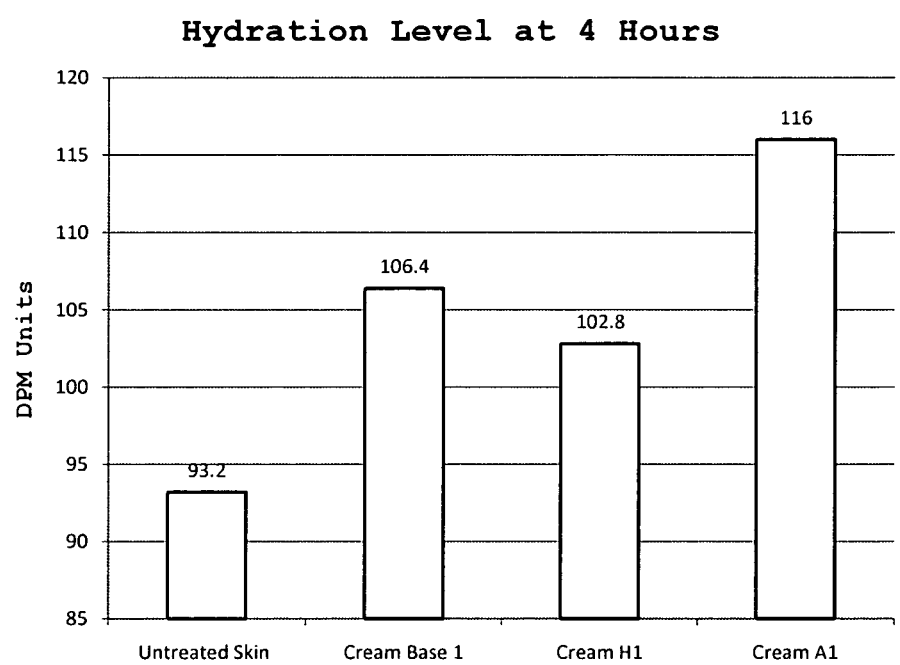
FIG. 1 illustrates a chart representing the moisturizing effect of 3% composition of the present invention in comparison with compositions comprising humectants and film formers on human skin, 4 hours after application.

A detailed illustrative embodiment of the present invention is disclosed herein. However, the present invention may be embodied in a wide variety of forms, some of which may be quite different from those in the disclosed embodiment. Consequently, the specific ingredients and functional details disclosed herein are merely representative, yet in that regard, they are deemed to afford the best embodiment for purposes of disclosure and to provide a basis for the claims herein which define the scope of the present invention.

Moreover, well known methods and procedures for both carrying out the objectives of the present invention and illustrating the preferred embodiment are incorporated herein by reference but have not been described in detail as not to unnecessarily obscure aspects of the present invention.

The cosmetic composition of the present invention improves skin texture, clarity, and skin tone by synergistic actions of a bio-chelated mineral blend and a humectant blend. The composition provides exceptional moisturization to the skin which lasts for an extended period of time. The hydrating effect of the composition is generally known to treat symptoms associated with dry skin such as itching, redness, fine lines, cracks, flaking, scaling, and peeling. The composition is also believed to tighten and brighten the skin and helps reduce the appearance of age related symptoms such as lines, wrinkles, and spots.

The composition of the present invention may be used alone or prepared into various forms including creams, lotions, gels, emulsions, sprays, sticks, powders, or the like. Depending on the consistency of the final composition, various containers may be suitable to store and dispense the composition.

It is contemplated that the cosmetic composition of the present invention is topically applied to the skin on any part of the mammalian body except mucous membrane. A suitable amount of the cosmetic composition can be applied using fingers, spatula, cotton swabs, facial cotton sheets, or any other application device known in the art.

The hydration and anti-aging benefits are achieved by combining up to approximately 1.0% by weight of a bio-chelated mineral blend and at least approximately 85.0% by weight of a humectant blend in the cosmetic composition. Preferably, the bio-chelated mineral blend is present in an amount from approximately 0.3% to approximately 0.9% by weight and the humectant blend is present in at least approximately 89.0% by weight in the cosmetic composition. It is the combination of the bio-chelated mineral blend and the humectant blend that offers the exceptional improvement in moisturization. The humectant blend works synergistically with the bio-chelated mineral blend to increase the hydration level of the skin. Once they penetrate into the epidermis, they draw moisture from the atmosphere, the deeper layers of epidermis, and the dermis.

The bio-chelated mineral blend is obtained by growing yeasts in an acidic culture medium suitable to support aerobic fermentation. Mineral salts of choice are added to the culture medium and fermentation is carried out until no free minerals are detected. At this time the cells of *Saccharomyces cerevisiae* are lysed by a method known in the art including detergent-based lysis, enzymatic lysis, mechanical disruption, liquid homogenization, sonication, freeze-thaw method, or manual grinding. Detergent-based or enzymatic lysis is especially useful to break open the cells without disrupting the protein content. Thereafter, any resulting insoluble material is filtered off. The remaining filtrate is then purified in a method known in the art to isolate the fraction containing minerals that are metabolically complexed with cellular glycoproteins.

Species of yeasts useful for obtaining the bio-chelated mineral blend include, but are not limited to any species of the genera *Saccharomyces* and *Pichia*. Nonlimiting examples of such species include *Saccharomyces bayanus, Saccharomyces boulardii, Saccharomyces cerevisiae, Saccharomyces pastorianus, Saccharomyces uvarum, Pichia acaciae, Pichia alni, Pichia americana, Pichia pastoris, Pichia amethionina, Pichia amylophila, Pichia angophorae, Pichia angusta, Pichia anomala, Pichia populi, Pichia stipitis, Pichia toletana, Pichia xylosa, Pichia Onychis,* and *Pichia salicaria*. In a preferred embodiment, the bio-chelated mineral blend comprises extracts of *Saccharomyces cerevisiae*, a species of budding yeast.

Minerals that may comprise the bio-chelated mineral blend are those that contain, but are not limited to silicon, magnesium, copper, iron, zinc, calcium, phosphorus, sodium, potassium, chloride, sulfur, iodine, manganese, fluorine, cobalt, chromium, molybdenum, and selenium.

It is known that certain minerals, including magnesium and zinc, govern several biological parameters of yeast including the rate of fermentation, the degree of attenuation, and types of biomolecules produced. (Graeme M. Walker, et al., *Yeast-Metal Interactions: Impact on Brewing and Distilling Fermentations*, Institute of Brewing & Distilling Asia Pacific Section 2006 Convention, Hobart, Australia (Mar. 19-24, 2006)). Therefore, the presence or lack of certain minerals during fermentation significantly impacts the resulting composition of yeast extracts. Consequently, the molecular make up of bio-chelated mineral blend and its benefits are unique for each mineral used to culture yeasts. Thus, no two different bio-chelated mineral blends provide the exact same effect on the mammalian skin.

In a preferred embodiment, bio-chelated mineral blend consists essentially of a combination of *Saccharomyces* zinc ferment, *Saccharomyces* copper ferment, *Saccharomyces* magnesium ferment, *Saccharomyces* iron ferment, *Saccharomyces* silicon ferment, and *Saccharomyces* calcium ferment. More preferably, each bio-chelated mineral is present in equal parts by weight. This exact combination of bio-chelated mineral blend, in conjunction with humectant blend, provides an unexpected moisturizing effect on mammalian skin. The preferred bio-chelated mineral blend is available from Active Concepts LLC (Piscataway, N.J.).

Preferably, the bio-chelated mineral blend comprises from approximately 0.05% to approximately 0.15% by weight of *Saccharomyces* calcium ferment. *Saccharomyces* calcium ferment is obtained by growing *Saccharomyces cerevisiae* in an acidic, nutrient-enriched medium containing calcium minerals while facilitating aerobic fermentation. *Saccharomyces* calcium ferment is believed to penetrate the skin more readily than its counterpart calcium minerals. A certain calcium level in the epidermis is essential, as it is believed to regulate cell turnover and lipid barrier functions via cell differentiation. It is also believed that increased epidermal calcium level stimulates rapid cell turnover. (Andrzej A. Dlugosz, et al., *Protein Kinase C Regulates Keratinocyte Transglutaminase ($TG_k$) Gene Expression in Cultured Primary Mouse Epidermal Keratinocytes Induced to Terminally Differentiate by Calcium*, Journal of Investigative Dermatology, 102; 409-414 (1994)). Therefore, the process of cell turnover can be enhanced with absorbable topical calcium, such as *Saccharomyces* calcium ferment, resulting in plumper looking skin.

Preferably, the bio-chelated mineral blend further comprises from approximately 0.05% to approximately 0.15% by weight of *Saccharomyces* silicon ferment. *Saccharomyces* silicon ferment is obtained by growing *Saccharomyces cerevisiae* in an acidic, nutrient-enriched medium containing silicon minerals while facilitating aerobic fermentation. *Saccharomyces* silicon ferment is believed to penetrate the skin more readily than its counterpart silicon minerals. Topically applied silicon (Si) is usually produced in the form of silicone ($[R_2SiO]_n$). One study shows that when grafted meshed skin was treated by topical silicone cream, the site showed less hardness and better appearance of the skin in all patients compared with the control site, which was treated by application of petroleum jelly ointment (i.e., a film former). (Y. Sawada, et al., *Benefits of Silicone Occlusive Dressing for Treatment of Meshed Skin Grafts*, Burns, 18(3); 233-6 (June, 1992)). In a separate study, silicone cream occlusive treatment was performed on 27 patients with skin grafts. This resulted in significantly less pigmentation and hardness in 21 patients, less marginal scar hypertrophy in 10 patients, and less redness in 7 patients. In 9 cases, fewer wrinkles resulted in the silicone cream treated lesion. (Y. Sawada, et al., *Beneficial Effects of Silicone Cream on Grafted Skin*, British Journal of Plastic Surgery, 45(2):105-8 (February-March, 1992)).

Preferably, the bio-chelated mineral blend further comprises from approximately 0.05% to approximately 0.15% by weight of *Saccharomyces* magnesium ferment. *Saccharomyces* magnesium ferment is obtained by growing *Saccharomyces cerevisiae* in an acidic, nutrient-enriched medium containing magnesium minerals while facilitating aerobic fermentation. *Saccharomyces* magnesium ferment is believed to penetrate the skin more readily than its counterpart magnesium minerals. Magnesium is a major component of the Dead Sea water, which is known for its therapeutic effects on the skin. The presence of magnesium in the skin is also believed to slow down the ageing process in the skin and is required in hundreds of key biochemical processes in the human body. It also stimulates the skin to ensure that healthy elasticity is maintained and moisture levels remain normal. Magnesium sulfate can also be absorbed into the skin, reducing inflammation. The topical use of magnesium in the form of magnesium chloride in a cream has also been suggested as an alternative to commonly used corticosteroids for treating common skin diseases. (P. W. M. Copeman., et al., *New Non-Steroid Non-Antibiotic Skin Medicaments*, British Medical Journal, 4:264 (Nov. 1, 1975)).

In the preferred embodiment, the bio-chelated mineral blend further comprises from approximately 0.05% to approximately 0.15% by weight of *Saccharomyces* copper ferment. *Saccharomyces* copper ferment is obtained by growing *Saccharomyces cerevisiae* in an acidic, nutrient-enriched medium containing copper minerals while facilitating aerobic fermentation. *Saccharomyces* copper ferment is believed to penetrate the skin more readily than its counterpart copper minerals. Together with vitamin C and the mineral zinc, absorbable copper helps to develop elastin, the fibers that support skin integrity. Copper is a key component of the enzyme tyrosinase, which is necessary for the production of melanin by activation of the melanocytes. Topically applied lipophilic copper complexes (e.g. copper salicylate) significantly penetrate the skin, offering anti-inflammatory and anti-arthritic benefits. (S. J. Beveridge, et al., Lipophilic Copper (II) Formulations: *Some Correlations Between Their Composition and Anti-Inflammatory/Anti-Arthritic Activity When Applied to the Skin of Rats*, Agents and Actions, vol. 12, 1/2 (1982)). The presence of Cu(II) in these complexes is considered essential for their efficacy.

Preferably, the bio-chelated mineral blend further comprises from approximately 0.05% to approximately 0.15% by weight of *Saccharomyces* iron ferment. *Saccharomyces* iron ferment is obtained by growing *Saccharomyces cerevisiae* in an acidic, nutrient-enriched medium containing iron minerals while facilitating aerobic fermentation. *Saccharomyces* iron ferment is believed to penetrate the skin more readily than its counterpart iron minerals. Iron is essential for Deoxyribonucleic acid (DNA) and Ribonucleic acid (RNA) synthesis, electron transport, and oxygen metabolism. Recent studies suggest that a sufficient amount of absorbable iron may facilitate elastin production in the skin by increasing elastin messenger RNA (mRNA) level (Bunda, et al., *Fluctuations of Intracellular Iron Modulate Elastin Production*, The Journal of Biological Chemistry, 280, 2341-2351 (Jan. 21, 2005)).

In the preferred embodiment, the bio-chelated mineral blend further comprises from approximately 0.05% to approximately 0.15% by weight of *Saccharomyces* zinc ferment. *Saccharomyces* zinc ferment is obtained by growing *Saccharomyces cerevisiae* in an acidic, nutrient-enriched medium containing zinc minerals while facilitating aerobic fermentation. *Saccharomyces* zinc ferment is believed to penetrate the skin more readily than its counterpart zinc minerals. Zinc takes part in the structural role in superoxide dismutase, an antioxidant enzyme. It also plays a role in biochemical reactions of the extra-cellular matrix, while enhancing cell division, repair and growth. (Elizabeth F. Rostan, et al, *Evidence Supporting Zinc as an Important Antioxidant for skin*, International Journal of Dermatology, 41(9): 606-611 (September, 2002)). For example, zinc serves as a co-factor in the skin's production of certain metalloproteinases that remove damaged or mutated tissue. The study of skin injuries has shown that an injured site becomes saturated with zinc, which facilitates the regeneration of epidermis. (M. Iwata, et al., *Zinc Accumulation and Metallothionein Gene Expression in the Proliferating Epidermis During Wound Healing in Mouse Skin*, Histochemistry and Cell Biology, 112(4): 283-290 (October, 1999)). The inefficiency of wound healing in elderly people is frequently related to inadequate zinc-injury response. Thus, topical zinc in the form of *Saccharomyces* zinc ferment is thought to stimulate biochemical reactions that are essential for healthy skin.

The cosmetic composition of the present invention further comprises a humectant blend. The humectant blend may comprise one type of humectant or a mixture of various types of humectants. Preferably, at least one humectant is a plant/fungus/fruit extract and at least one humectant is a polysaccharide.

In addition to their hydrating effects, certain humectants are known to provide supplementary benefits to the skin. For example, it is suggested that when applied topically, glycerin may be capable of stimulating lipid synthesis, wound healing, and regulating keratinocyte function. (Xiangjian Zheng, et al., *Aquaporin 3 Colocates with Phospholipase $D_2$ in Caveolin-Rich Membrane Microdomains and is Downregulated upon Keratinocyte Differentiation*, Journal of Investigative Dermatology, 121, 1487-1495 (2003)). Some plant extracts, including *Beta vulgaris* (beet) root extract, are capable of inhibiting one or more extracellular proteases, thereby acting as anti-aging agents. (See U.S. patent application Ser. No. 10/533,025). Polysaccharides, in general, are known to reduce the tack associated with common humectants. Therefore, a preferred humectant blend comprises at least one humectant selected from the group consisting of glycerin, *Beta vulgaris* (beet) root extract, and polysaccharides. A particularly preferred humectant blend comprises from approximately 70.70% to approximately 78.9% by weight of glycerin, from approximately 18.0% to approximately 22.0% by weight of *Beta vulgaris* (beet) root extract, and from approximately 1.0% to approximately 3.0% by weight of *Aloe barbadensis* leaf polysaccharides.

Examples of other humectants that are suitable to comprise the humectant blend include, but are not limited to *Aloe barbadensis* leaf extract, *Aloe andongensis* leaf juice, *Aloe andongensis* extract, *Albatrellus confluens* extract, *Averrhoa carambola* leaf extract, *Backhousia anisata* leaf extract, *Banksia spinulosa* flower extract, *Bidens pilosa* extract, *Ceramium rubrum* extract, *Citrus auratium Tachibana* peel extract, *Cnidium monnieri* fruit extract, *Cocos nucifera* fruit juice, *Coleus scutellarioides* extract, *Convolvulus arvensis* extract, *Dunaliella bardawill* extract, *Echium lycosis* root extract, *Entada phaseoloides* leaf extract, *Erica canaliculata* extract, *Ficus carica* (fig) fruit extract, *Ganoderma atrum* extract, *Ganoderma neo-japonicum* extract, *Gentiana pros-*

*trate* extract, *Glycyrrhiza glabra* (licorice) root extract, *Legenaria siceraria* fruit extract, *Lantana camara* root extract, *Larix europaea* wood extract, *Lepidium meyenii* root extract, *Lespedeza bicolor* bark extract, *Lycopodium clavatum* extract, *Macrotomia euchroma* root extract, *Magnolia kobus* bark extract, *Momordica charantia* fruit extract, *Momordica grosvenori* fruit juice, *Paulownia tomentosa* leaf extract, *Phalaenopsis amabillis* extract, *Phaseolus trilobus* seed extract, *Portulaca grandiflora* extract, *Portulaca oleracea* extract, *Primula sikkimensis* flower extract, *Prostanthera incise* leaf extract, *Prunus persica* bud extract, *Pueraria lobata* root extract, *Ribes nigrum* seed extract, *Rosa rugosa* leaf extract, *Saussurea involucrata* extract, *Scutellaria baicalensis* root extract, *Sesamum indicum* sprout extract, *Simmondsia chinensis* (jojoba) leaf extract, honey extract, albumen extract, algae oligosaccharides, agarose, lactose, jellyfish extract, fructose, fructan, diglycerin, propylene glycol, glucose, acetamide MEA, acetyl histidine, anserine, calcium fructoborate, cellulose succinate, choline chloride, erythritol, ethyl glucoside, corn glycerides, 1,3-butylene glycol, hydrolyzed corn starch, hydroxylated jojoba oil, lactic acid, lysine PCA, polyglucuronic acid, sodium PCA, sorbitol, maltose, mannitol, mannose, maltitol, melibiose, urea, dimethyl imidazolidinone, sodium hyaluronate, xylitol, xylose, and mixtures thereof.

The composition of the present invention may further comprise one or more vitamins and/or antioxidants selected from the group consisting of vitamin A (e.g., retinyl palmitate) and their derivatives, vitamin B1 (e.g., thiamine) and their derivatives, vitamin B2 (e.g., riboflavin) and their derivatives, vitamin B3 (e.g., niacin or nicotinamide) and their derivatives, vitamin B5 (e.g., pantothenic acid) and their derivatives, vitamin B6 (e.g., pyridoxine, pyridoxal, or pyridoxamine) and their derivatives, vitamin B12 (e.g., cyanocobalamin) and their derivatives, vitamin C (e.g., ascorbic acid) and their derivatives, vitamin E (e.g., tocopherol acetate) and their derivatives, vitamin H (e.g., biotin) and their derivatives, vitamin K (e.g., phytonadione) and their derivatives, and vitamin M (e.g., folic acid) and their derivatives, ubiquinone (also known as coenzyme Q10), glutathione, melatonin, resveratrol, citric acid, gallic acid and its esters, nordihydroguaiaretic acid, lipoic acid, dihydrolipoic acid, glycolic acid, alpha-arbutin, chitosan salicylate, rosmarinic acid, green tea extract, smithsonite extract, *Angelica archangelica* extract, *Camellia sinensis* extract, Coffee Arabica extract, *Pongamia pinnata* extract, and mixtures thereof. Most preferably, vitamin A, vitamin C, vitamin B5, and ubiquinone are used in the present invention. Vitamins A and C have strong antioxidative properties that complement the effects of ubiquinone. Topical application of vitamin B5 in the form of pantothenic acid helps maintain proper levels of endogenous lipids to prevent TEWL.

The composition of the present invention may further comprise a copper mineral, known as azurite ($Cu_3(CO_3)_2(OH)_2$). The presence of additional minerals enhances the moisturizing effect of the composition. The mineral comprises copper, which improves the skin's elasticity by enhancing elastin formation. Additionally, azurite imparts a vivid blue color. Given the vastly growing trends of water and hydrating products in cosmetics, using minerals that inspire images of deep oceanic blue is an effective marketing strategy. Thus, it is desirable to include a mineral that can also serve as a colorant. Other minerals that may comprise the composition of the present invention include, but not limited to ferrous oxide (FeO), ferric oxide ($Fe_2O_3$), chromium oxide greens ($Cr_2O_3$), chromium hydroxide greens ($Cr_2O_3.2H_2O$), sodium aluminum sulfosilicates ($Na_y(Al_wSi_xO_y)S_z$ with proportions of each component depending on the desired color), titanium dioxide ($TiO_2$), manganese violet ($MnNH_4P_2O_7$), and mixtures thereof.

The composition of the present invention may further comprise *Leuconostoc* radish root ferment filtrate. It is a filtrate of the product obtained by the fermentation of *Raphanus sativus* roots by the microorganism, *Leuconostoc*. This ingredient provides antimicrobial functions, thus acting as a preservative. Other preservatives that are suitable for use in the present invention include, but are not limited to *Candida Bombicola*/glucose/methyl rapeseedate ferment, *Albizia lebbek* leaf, *Asparagus racemosus* root, *Asparagus racemosus* root extract, *Melia azadirachta* bark extract, *Phyllanthus Niruri* extract, *Pinus Pinaster* bark extract, *Rosmarinus officinalis* leaf extract, *Terminalia bellerica* fruit extract, *Vitis vinifera* seed extract, *Citrus grandis* fruit extract, *Citrus grandis* seed extract, benzalkonium chloride, betaine salicylate, dibromocyanoacetamide, dodecyltriphenylphosphonium bromide, hexylresorcinol, methylbenzethonium chloride, oligopeptide-3, cresol, camphor, formaldehyde, isopropylparaben, magnesium benzoate, and mixtures thereof.

The invention may further include other agents that are commonly used in cosmetic compositions. Examples of such ingredients include, but are not limited to skin conditioning agents, film formers, sun screens, viscosity increasing agents, and fragrance.

The composition of the present invention may comprise one or more skin conditioning agents. Non-limiting examples of skin conditioning agents include allantoin, biosaccharide gum, bisabolol, oligopeptides, dimethicone crosspolymer, beta-glucan, sunflower seed oil, linoleic acid, niacin, niacinamide, phospholipids, hydrolyzed soy protein, soy sterol, soy amino acids, sodium hyaluronate, tyrosine, wheat amino acids, and mixtures thereof.

The composition of the present invention may comprise one or more film formers. Non-limiting examples include petrolatum, dimethicone, Balsam Canada resin, acrylamide/ammonium acrylate copolymer, butadiene/acrylonitrile copolymer, bis-stearyl dimethicone, dimethicone PEG-8 polyacrylate, ethylene acrylic acid copolymer, polymethylglutamate, polyquaternium-1, polyquaternium-2, polyquaternium-4, polyquaternium-8, polyquaternium-12, polyquaternium-62, styrene/VP copolymer, TEA-diricinoleate/IPDI copolymer, polybutylene terephthalate, and mixtures thereof.

The composition of the present invention may comprise one or more sunscreens. A wide variety of sun screening agents are described in U.S. Pat. Nos. 5,073,371 and 5,073,372. Non-limiting examples of sunscreens are 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, octyl salicylate, 4,4'-methoxy-t-butyldibenzolymethane, 3-benzylidene camphor, titanium dioxide, zinc oxide, iron oxide, and mixtures thereof.

The composition of the present invention may comprise one or more viscosity increasing agents. Viscosity increasing agents can be both aqueous and non-aqueous. Non-limiting examples include acrylamides copolymer, acrylamide/sodium acrylate copolymer, acrylates/alkyl acrylate crosspolymer, beewax, carbomer, cetearyl alcohol, hydrogenated vegetable oils, hydropropyl starch phosphate, magnesium silicate, polyvinyl alcohol, sodium chloride, xanthan gum and mixtures thereof.

The composition of the present invention may comprise one or more fragrances. Non-limiting examples include amyl benzoate, anethole, anise alcohol, benzyl laurate, bisabolol, butoxydiglycol, butyl stearate, camphor, carmine, dimethyl decadienal, isoamyl acetate, lauryl alcohol, *Lavandula angustifolia* extract, limonene, linalool, methoxyindane, methyl caprylate, *Narcissus poeticus* extract, and mixtures thereof.

The following examples further describe and demonstrate embodiments within the scope of the present invention. The examples are given solely for the purpose of illustration and are not to be construed as limitations of the present invention, as many variations are possible without departing from the spirit and scope of the invention.

Example 1

| Ingredients | Concentration range (w/w %) |
| --- | --- |
| Glycerin | 70.70-78.90 |
| Beet Root Extract | 18.00-22.00 |
| *Aloe Barbadensis* Leaf Polysaccharides | 1.00-3.00 |
| Retinol | 0.05-0.15 |
| Ascorbic Acid | 0.05-0.15 |
| Tocopherol Acetate | 0.05-0.15 |
| Pantothenic Acid | 0.05-0.15 |
| *Saccharomyces* Zinc Ferment | 0.05-0.15 |
| *Saccharomyces* Copper Ferment | 0.05-0.15 |
| *Saccharomyces* Magnesium Ferment | 0.05-0.15 |
| *Saccharomyces* Iron Ferment | 0.05-0.15 |
| *Saccharomyces* Silicon Ferment | 0.05-0.15 |
| *Saccharomyces* Calcium Ferment | 0.05-0.15 |
| Ubiquinone | 0.05-0.15 |
| Azurite | 0.05-0.15 |
| *Leuconostoc*/Radish Root Ferment Filtrate | 1.50-2.50 |

Example 2

| Ingredients | Weight Percent (w/w %) |
| --- | --- |
| Glycerin | 74.80 |
| Beet Root Extract | 20.00 |
| *Aloe Barbadensis* Leaf Polysaccharides | 2.00 |
| Retinol | 0.10 |
| Ascorbic Acid | 0.10 |
| Tocopherol | 0.10 |
| Pantothenic Acid | 0.10 |
| *Saccharomyces* Zinc Ferment | 0.10 |
| *Saccharomyces* Copper Ferment | 0.10 |
| *Saccharomyces* Magnesium Ferment | 0.10 |
| *Saccharomyces* Iron Ferment | 0.10 |
| *Saccharomyces* Silicon Ferment | 0.10 |
| *Saccharomyces* Calcium Ferment | 0.10 |
| Ubiquinone | 0.10 |
| Azurite | 0.10 |
| *Leuconostoc*/Radish Root Ferment Filtrate | 2.00 |
| Total | 100.00 |

The compositions in Examples 1 and 2 are prepared in a conventional manner known in the art. They may be used alone or incorporated in a final cosmetic product in various forms including creams, lotions, gels, emulsions, sprays, sticks, powders, or the like. In a cream or a lotion composition, the composition as shown in Examples 1 or 2 may be preferably used in at least around 1% by weight of the final cream/lotion composition. More preferably, the final cream/lotion composition comprises at least approximately 3% by weight of the Example 2 composition.

Example 3

Demonstration of Hydration Effect of Example 2 Composition Compared to a Composition containing Humectants and a Film Former The composition according to Example 2 was tested to demonstrate its moisturizing ability on the stratum corneum. Hydration level of the stratum corneum can be quantified by evaluating its electrical properties, in particular, its impedance (Z). This is based on a general principle that electrical conduction increases with increase in hydration. Dry stratum corneum has very low electrical conduction due to the low dielectric constants of its lipid constituents. The equation below shows the relationship between impedance (Z), resistance (R) and capacitance (C) in a model that depicts the skin as a resistor and capacitor connected in parallel:

$$Z=[R^2+(1/2\Pi fC)^2]^{1/2} \qquad (1)$$

wherein f is the frequency of the applied alternating current.

The instrument used in the tests is the Nova Dermal Phase Meter (DPM) 9003 available from Nova technologies Corporation (Gloucester, Mass.). The standard probe that comes with the instrument is applied to the skin with a constant application pressure. Nova DPM 9003 emits a 1-MHz span of simultaneously produced frequencies, producing a differential current source with a controlled rise time. Impedance is evaluated at several frequencies using a proprietary chip in the instrument. Values are reported as arbitrary units ranging from 90 to 999 DPM. A higher value indicates higher moisturization of the stratum corneum.

In the first moisturization study, the composition of Example 2 ("Composition A") was compared to DayMoist CLR ("Composition H") available from Chemisches Laboratorium Dr. Kurt Richter GmbH. Composition H primarily contains humectants including hydrolyzed starch and beet root extract, and no film formers. Compositions A and H were also incorporated in a cream base ("Cream Base 1") at 3% by weight to form cream compositions ("Cream A1" and "Cream H1", respectively). Cream Base 1 is Vaseline Intensive Care™ Advanced Healing Lotion, comprising film formers (i.e., petrolatum and dimethicone) and humectant (i.e., glycerin). Table 1 below summarizes all samples prepared for the study. Each sample was tested on five subjects on their volar forearms for a period of 8 hours.

TABLE 1

| Sample Name | Description of Samples |
| --- | --- |
| Composition A | 100% Example 2 Composition |
| Composition H | DayMoist CLR available from Chemisches Laboratorium Dr. Kurt Richter GmbH |
| Cream Base 1 | Vaseline Intensive Care ™ Advanced Healing Lotion available from Unilever |
| Cream A1 | 3% Example 2 Composition in Cream Base 1 |
| Cream H1 | 3% Composition H in Cream Base 1 |

The area of test sites on each subject consisted of seven randomized 3 cm×3 cm sections. Prior to the commencement of the test, the subjects participated in a 3 day dry-blown phase. Fifteen minutes prior to the initial recording of data, the subjects were allowed to acclimate to the testing environment at 70±3° F. with a relative humidity of 40±10%. The first recording measured baseline moisture values (Baseline). The initial dose of each sample was then applied immediately after the baseline measurements were taken. A 2 mg/cm$^2$ dose of each sample was applied to each test site (i.e., 18 mg per site) and rubbed in for 10 seconds with a gloved finger. The assignment of samples on testing sites was randomized. Measurements were again recorded at 4 and 8 hours after application. All measurements were taken in triplicates with Nova DPM 9003. Measurements were also taken for an untreated control test site (Untreated Skin) on each subject. Table 2 below summarizes the moisturizing effect of each tested sample on the stratum corneum, measured in DPM units.

TABLE 2

|  | Baseline (DPM) | 4 hours (DPM) | 8 hours (DPM) |
| --- | --- | --- | --- |
| Composition A | 92.0 | 134.6 | 125.6 |
| Composition H | 92.4 | 95.6 | 105.2 |
| Cream A1 | 92.4 | 116 | 116.4 |
| Cream H1 | 92.4 | 102.8 | 106.0 |
| Cream Base 1 | 92.4 | 106.4 | 105.6 |
| Untreated Skin | 92.4 | 93.2 | 94.8 |

Figure 2:
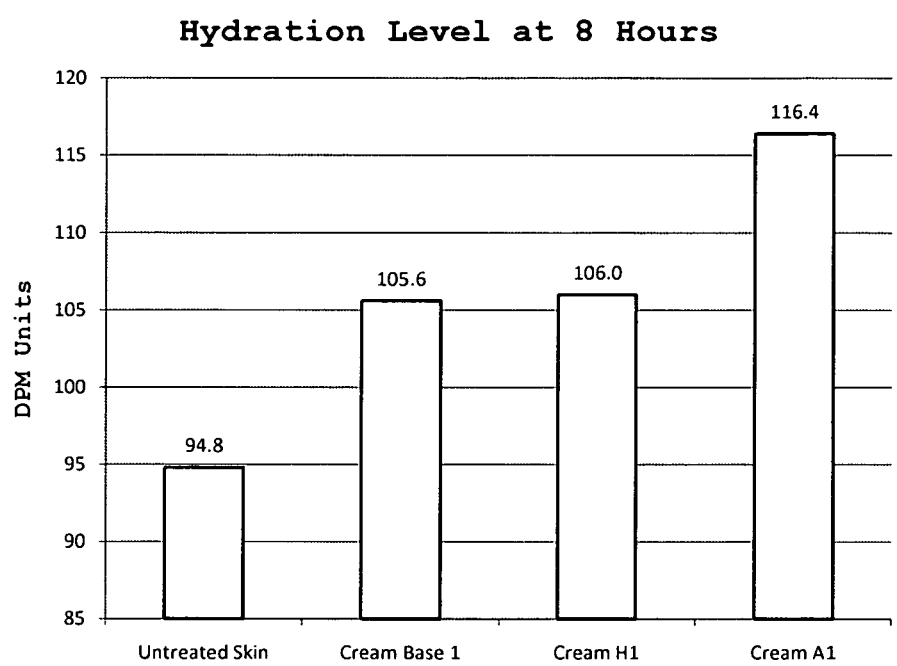
FIG. 2 illustrates a chart representing the moisturizing effect of 3% composition of the present invention in comparison with compositions comprising humectants and film formers on human skin, 8 hours after application.

FIGS. 1 and 2 demonstrate the hydration ability of 3% of Example 2 composition (Composition A) in Cream Base 1 (Cream A1) compared to 3% of Composition H in Cream Base 1 (Cream H1) and Cream Base 1. FIG. 1 shows hydration levels of each sample at 4 hours after application, and FIG. 2 shows hydration levels at 8 hours after application. As apparent from both Figures, measured values for Cream A1 at 4 and 8 hours are consistently around 116 DPM. Furthermore, the differences in DPM values between Cream A1 and Cream H1 are apparent, as are for Cream A1 and Cream Base 1. Specifically, Cream A1 is consistently at least 9% higher in DPM value than Cream H1 or Cream Base 1 at both 4 and 8 hours after application.

Figure 3:
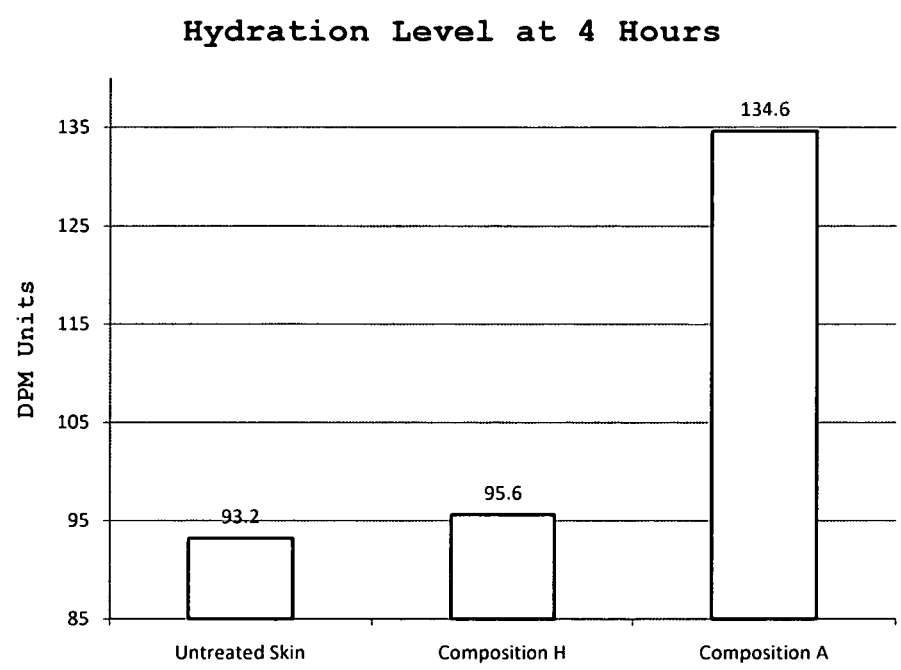
FIG. 3 illustrates a chart representing the moisturizing effect of 100% composition of the present invention in comparison with compositions comprising humectants and film formers on human skin, 4 hours after application.
Figure 4:
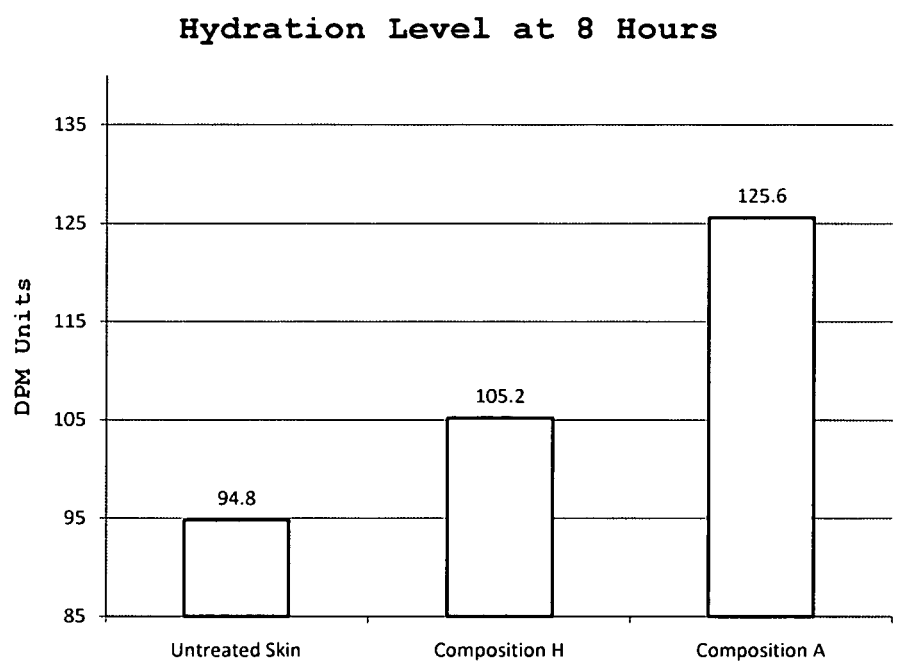
FIG. 4 illustrates a chart representing the moisturizing effect of 100% composition of the present invention in comparison with compositions comprising humectants and film formers on human skin, 8 hours after application.

FIGS. 3 and 4 show the hydration ability of 100% of Example 2 composition (Composition A) compared with Composition H at 4 hours and 8 hours after application. As shown, the DPM values obtained by Composition A exceed those of Composition H by at least 19%. Moreover, it is apparent from FIGS. 1, 2, 3, and 4 that DPM values generally increase with increasing concentration of Example 2 composition in a sample. Interestingly, the same generalization cannot be made for Composition H, which contains humectants and no film formers. Specifically, the DPM value for Cream H1 (i.e., 3% Composition H in Cream Base 1) is 102.8 DPM at 4 hours in FIG. 1, whereas the DPM value for 100% Composition H is merely 95.6 DPM at 4 hours as shown in FIG. 3. Cream H1 and Composition H both increase in their DPM values at 8 hours as shown in FIGS. 2 and 4, respectively, but the highest DPM value achieved by Composition H (i.e., 105.2 DPM) is not considerably different from the highest value achieved by Cream H1 (i.e., 106 DPM).

The results shown in FIGS. 1, 2, 3, and 4 suggest that a composition containing bio-chelated mineral blend and humectant blend hydrates the stratum corneum more effectively than a composition comprising a film former and a humectant (i.e., Cream H1 and Cream Base 1) or humectants alone (i.e., Composition H). Furthermore, the results demonstrate that an increase in the concentration of Composition A enhances the hydrating effect on the skin.

Example 4

Demonstration of Hydration Effect of Example 2 Composition Compared to a Composition with a Different Blend of Bio-Chelated Minerals In the second moisturization study, the composition of Example 2 was prepared at concentrations of 1% ("Cream B2") and 3% ("Cream A2") by weight in a cream platform base as described in Table 3 ("Cream Base 2"). Cream B2 and Cream A2 were compared with TransformEssence ("Cream C") available from Saint Germain Cosmetics. Cream C is a cream composition comprising humectants, *Saccharomyces* copper ferment, *Saccharomyces* manganese ferment, and *Saccharomyces* zinc ferment. The humectants in Cream C are hyaluronic acid, beet root extract, glycerin, and *Aloe barbadensis* leaf juice. Table 4 summarizes all samples tested in the study. Each sample was tested on five subjects on their volar forearms for a period of 12 hours.

TABLE 3

| Cream Base 2 Ingredients | Weight Percent (w/w %) |
| --- | --- |
| Water | 77.4 |
| Carbomer | 0.15 |
| Disodium EDTA | 0.03 |
| Tetrasodium EDTA | 0.05 |
| Methylparaben | 0.15 |
| Glycerin | 5.70 |
| *Aloe Barbadensis* Leaf Juice | 0.10 |
| Isododecane | 1.40 |
| Neopentyl Glycol Diheptanoate | 0.60 |
| Petrolatum | 3.00 |
| Cetyl Alcohol | 2.50 |
| Cetearyl Alcohol | 2.48 |
| Ceteareth-20 | 1.92 |
| Propylparaben | 0.05 |
| Tocopherol Acetate | 0.01 |
| *Macadamia Ternifolia* Seed Oil | 0.05 |
| Dimethicone | 2.00 |
| Sodium Hydroxide | 0.05 |
| Benzyl Alcohol | 0.10 |
| Propylene Glycol | 0.02 |
| *Avena Sativa* (Oat) Kernel Extract | 0.01 |
| *Viola Odorata* Extract | 0.01 |
| Ascorbic Acid | 0.01 |
| Diazolidinyl Urea | 0.20 |
| Fragrance | 2.00 |
| Total | 100 |

TABLE 4

| Sample Name | Description of Samples |
| --- | --- |
| Cream A2 | 3% Example 2 in Cream Base 2 |
| Cream B2 | 1% Example 2 in Cream Base 2 |
| Cream C | TransformEssence available from Saint Germain Cosmetics |
| Cream Base 2 | See Table 3 |

The area of test sites on each subject consisted of four randomized 3 cm×3 cm sections. Prior to the commencement of the test, the subjects participated in a 3 day dry-blown phase. Fifteen minutes prior to the initial recording of data, the subjects were allowed to acclimate to the testing environment at 70±3° F. with a relative humidity of 40±10%. The first recording measured baseline moisture values (Baseline). The initial dose of each sample was then applied immediately after the baseline measurements were taken. A 2 mg/cm$^2$ dose of each sample was applied to each test site (i.e., 18 mg per site) and rubbed in for 10 seconds with a gloved finger. The assignment of samples on testing sites was randomized. Measurements were again recorded at 4, 8, and 12 hours after application. All measurements were taken in triplicates with Nova DPM 9003 and the average values are obtained for each sample at each time point. Measurements were also taken for an untreated control test site (Untreated Skin) on each subject.

Table 5 below summarizes the moisturizing effect of each tested sample on the stratum corneum, measured in DPM units.

TABLE 5

|  | Baseline (DPM) | 4 hours (DPM) | 8 hours (DPM) | 12 hours (DPM) |
|---|---|---|---|---|
| Cream A2 | 93 | 118 | 118 | 114 |
| Cream B2 | 92 | 110 | 108 | 106 |
| Cream C | 92 | 104 | 106 | 102 |
| Untreated Skin | 92 | 92 | 94 | 92 |

Figure 5:
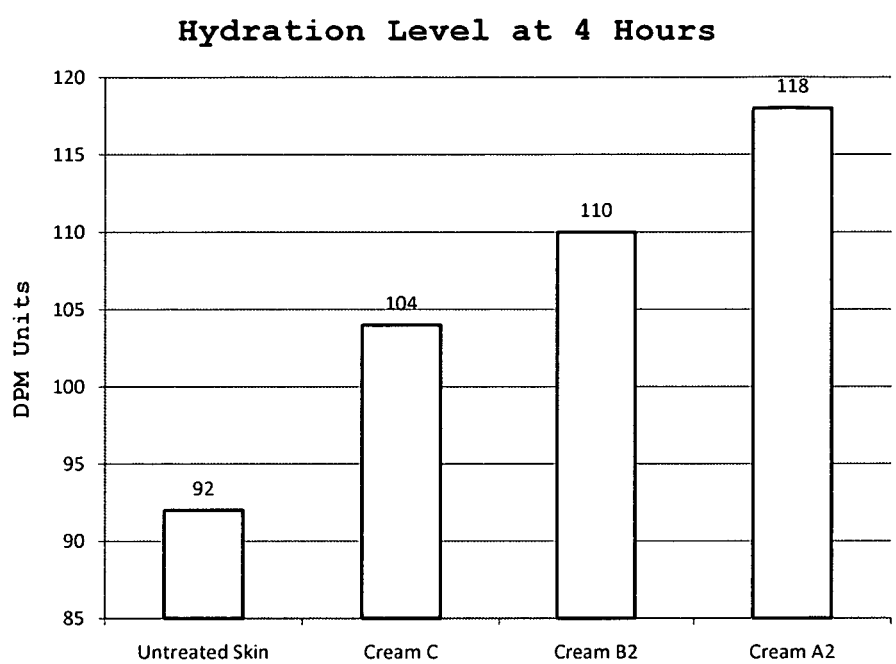
FIG. 5 illustrates a chart representing the moisturizing effect of compositions comprising bio-chelated mineral blend according to the present invention in comparison with a different blend of bio-chelated minerals on human skin, 4 hours after application.
Figure 6:
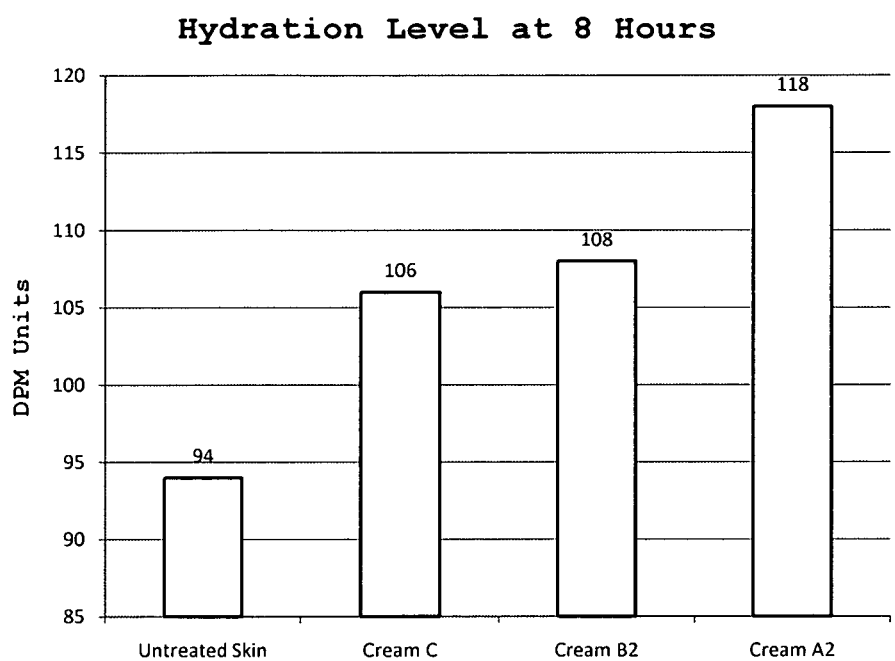
FIG. 6 illustrates a chart representing the moisturizing effect of compositions comprising bio-chelated mineral blend according to the present invention in comparison with a different blend of bio-chelated minerals on human skin, 8 hours after application.
Figure 7:
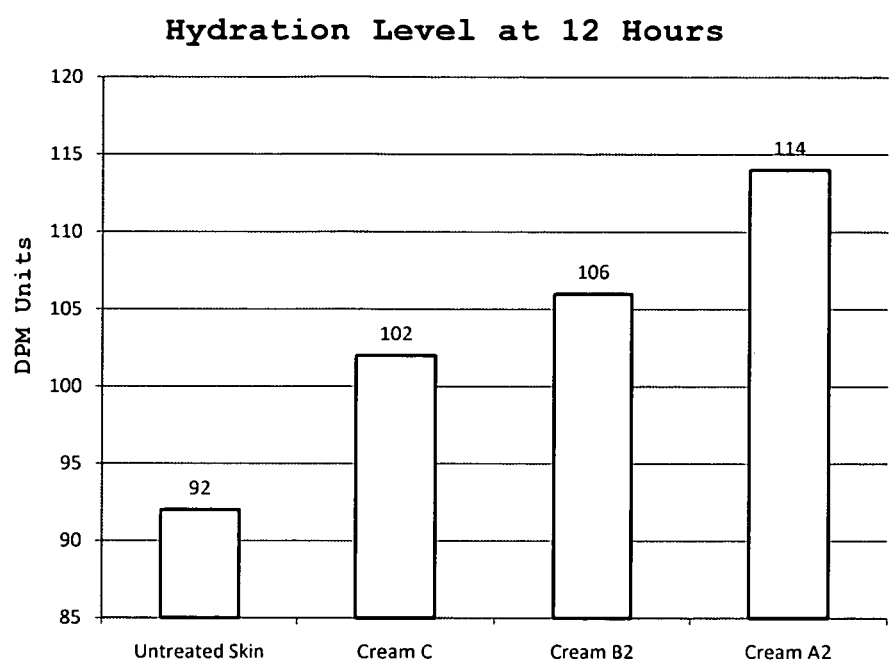
FIG. 7 illustrates a chart representing the moisturizing effect of compositions comprising bio-chelated mineral blend according to the present invention in comparison with a different blend of bio-chelated minerals on human skin, 12 hours after application.

The experimental results presented in FIGS. 5, 6, and 7 again demonstrate that the higher concentration of Example 2 composition (i.e., Cream A2) hydrates the skin more effectively compared to the lower concentration of Example 2 composition (i.e., Cream B2). Furthermore, DPM values of Creams A2 and B2 are consistently higher than Cream C throughout the 12 hour period. In particular, DPM values of Cream A2 are consistently above those of Cream C by at least 10%. These differences are statistically significant, as the two-tailed p-values for the difference between Cream A2 and Cream C are less than 0.01 throughout the first 12 hour period. Thus, we conclude that samples comprising the Example 2 composition (Creams A2 and B2) are better moisturizers than Cream C. Particularly, Cream A2 is able to hydrate the stratum corneum much more efficiently than Cream C.

The study significantly demonstrates that only certain combinations of bio-chelated minerals are able to achieve superior hydration of the stratum corneum. In this case, the mere incorporation of *Saccharomyces* copper ferment, *Saccharomyces* manganese ferment, and *Saccharomyces* zinc ferment in the composition containing humectants (i.e., Cream C) was not sufficient to achieve the same level of hydration as Creams A2 and B2.

While the present invention has been described with reference to the preferred embodiment and alternative embodiments, which have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the present invention is capable of being embodied in other forms without departing from its essential characteristics.

What is claimed is:

1. A cosmetic skin moisturizing composition comprising:
    approximately 70.7% to approximately 78.9% by weight of glycerin;
    approximately 18.0% to approximately 22.0% by weight of beet root extract;
    approximately 1.0% to approximately 3.0% by weight of *Aloe barbadensis* leaf polysaccharides;
    approximately 0.05% to approximately 0.15% by weight of retinol;
    approximately 0.05% to approximately 0.15% by weight of ascorbic acid;
    approximately 0.05% to approximately 0.15% by weight of tocopherol acetate;
    approximately 0.05% to approximately 0.15% by weight of pantothenic acid;
    approximately 0.05% to approximately 0.15% by weight of a yeast extract prepared from a *Saccharomyces* zinc ferment;
    approximately 0.05% to approximately 0.15% by weight of a yeast extract prepared from a *Saccharomyces* copper ferment;
    approximately 0.05% to approximately 0.15% by weight of a yeast extract prepared from a *Saccharomyces* magnesium ferment;
    approximately 0.05% to approximately 0.15% by weight of a yeast extract prepared from a *Saccharomyces* iron ferment;
    approximately 0.05% to approximately 0.15% by weight of a yeast extract prepared from a *Saccharomyces* silicon ferment;
    approximately 0.05% to approximately 0.15% by weight of a yeast extract prepared from a *Saccharomyces* calcium ferment;
    approximately 0.05% to approximately 0.15% by weight of ubiquinone;
    approximately 0.05% to approximately 0.15% by weight of azurite; and
    approximately 1.50% to approximately 2.50% by weight of *Leuconostoc*/radish root ferment filtrate.

2. The composition according to claim 1, wherein each yeast extract is present in equal amounts by weight.

3. The composition according to claim 1, comprising approximately 0.1% by weight of each yeast extract.

4. The composition according to claim 1, further comprising approximately 1.0% to approximately 3.0% by weight of *Aloe barbadensis* leaf extract.

5. The composition of claim 4, wherein said *Aloe* leaf extract is *Aloe barbadensis* leaf extract or *Aloe andongensis* leaf extract.

6. The composition according to claim 1, further comprising one or more ingredients selected from a group consisting of *Aloe andongensis* leaf extract, *Albatrellus confluens* extract, *Averrhoa carambola* leaf extract, *Backhousia anisata* leaf extract, *Banksia spinulosa* flower extract, *Bidens pilosa* extract, *Ceramium rubrum* extract, *Citrus auratium Tachibana* peel extract, *Cnidium Monnieri* fruit extract, *Cocos nucifera* fruit juice, *Coleus scutellarioides* extract, *Convolvulus arvensis* extract, *Dunaliella bardawill* extract, *Echium lycosis* root extract, *Entada phaseoloides* leaf extract, *Erica canaliculata* extract, *Ficus carica* (fig) fruit extract, *Ganoderma atrum* extract, *Ganoderma neo-japonicum* extract, *Gentiana prostrate* extract, *Glycyrrhiza glabra* (licorice) root extract, *Legenaria siceraria* fruit extract, *Lantana camara* root extract, *Larix europaea* wood extract, *Lepidium meyenii* root extract, *Lespedeza bicolor* bark extract, *Lycopodium clavatum* extract, *Macrotomia euchroma* root extract, *Magnolia kobus* bark extract, *Momordica charantia* fruit extract, *Momordica grosvenori* fruit juice, *Paulownia tomentosa* leaf extract, *Phalaenopsis amabillis* extract, *Phaseolus trilobus* seed extract, *Portulaca grandiflora* extract, *Portulaca oleracea* extract, *Primula sikkimensis* flower extract, *Prostanthera incise* leaf extract, *Prunus persica* bud extract, *Pueraria lobata* root extract, *Ribes nigrum* seed extract, *Rosa rugosa* leaf extract, *Saussurea involucrata* extract, *Scutellaria baicalensis* root extract, *Sesamum indicum* sprout extract, *Simmondsia chinensis* (jojoba) leaf extract, honey extract, albumen extract, algae oligosaccharides, agarose, lactose, jellyfish extract, fructose, fructan, diglycerin, propylene glycol, glucose, acetamide monoethanolamine (MEA), acetyl histidine, anserine, calcium fructoborate, cellulose succinate, choline chloride, erythritol, ethyl glucoside, corn glycerides, 1,3-butylene glycol, hydrolyzed corn starch, hydroxylated jojoba oil, lactic acid, lysine 5-Oxo-2-pyrrolidinecarboxylic acid (PCA), polyglucuronic acid, sodium 5-Oxo-2-pyrrolidinecarboxylic acid (PCA), sorbitol, maltose, mannitol, mannose, maltitol, melibiose, urea, dimethyl imidazolidinone, sodium hyaluronate, xylitol, xylose, and mixtures thereof.

7. The composition according to claim 1, further comprising vitamins selected from a group consisting of, vitamin B1, vitamin B2, vitamin B3, vitamin B6, vitamin B12, vitamin E, vitamin H, vitamin K, vitamin M, and combinations thereof.

8. The composition according to claim 1, further comprising antioxidants selected from a group consisting of glutathione, melatonin, resveratrol, citric acid, gallic acid and its esters, nordihydroguaiaretic acid, lipoic acid, dihydrolipoic acid, glycolic acid, alpha-arbutin, chitosan salicylate, rosmarinic acid, green tea extract, smithsonite extract, *Angelica archangelica* extract, *Camellia sinensis* extract, *Coffee Arabica* extract, *Pongamia pinnata* extract and mixtures thereof.

9. The composition according to claim 1, further comprising antioxidants selected from a group consisting of glutathione, melatonin, resveratrol, citric acid, gallic acid and its esters, nordihydroguaiaretic acid, lipoic acid, dihydrolipoic acid, glycolic acid and combinations thereof.

10. The composition according to claim 1, further comprising minerals selected from a group consisting of ferrous oxide, ferric oxide, chromium oxide greens, chromium hydroxide greens, sodium aluminum sulfosilicates, titanium dioxide, manganese violet and mixtures thereof.

11. A method for moisturizing skin or increasing hydration of skin or reducing the appearance of skin aging; wherein said method comprises topically applying the composition of claim 1 to the skin of a subject in need thereof.

12. A cosmetic skin moisturizing composition comprising:
approximately 74.8% by weight of glycerin;
approximately 20.0% by weight of beet root extract;
approximately 2.0% by weight of *Aloe* leaf approximately polysaccharides;
approximately 0.1% by weight of retinol;
approximately 0.1% by weight of ascorbic acid;
approximately 0.1% by weight of tocopherol acetate;
approximately 0.1% by weight of pantothenic acid;
approximately 0.1% by weight of a yeast extract prepared from a *Saccharomyces* zinc ferment;
approximately 0.1% by weight of a yeast extract prepared from a *Saccharomyces* copper ferment;
approximately 0.1% by weight of a yeast extract prepared from a *Saccharomyces* magnesium ferment;
approximately 0.1% by weight of a yeast extract prepared from a *Saccharomyces* iron ferment;
approximately 0.1% by weight of a yeast extract prepared from a *Saccharomyces* silicon ferment;
approximately 0.1% by weight of a yeast extract prepared from a *Saccharomyces* calcium ferment;
approximately 0.1% by weight of ubiquinone;
approximately 0.1% by weight of azurite; and
approximately 2.0% by weight of *Leuconostoc*/radish root ferment filtrate.

* * * * *